(12) United States Patent
Mercep et al.

(10) Patent No.: US 7,312,203 B2
(45) Date of Patent: Dec. 25, 2007

(54) 1-AZA-DIBENZOAZULENES AS INHIBITORS OF TUMOUR NECROSIS FACTOR PRODUCTION AND INTERMEDIATES FOR THE PREPARATION THEREOF

(75) Inventors: Mladen Mercep, Zagreb (HR); Milan Mesic, Zagreb (HR); Dijana Pesic, Sibenik (HR)

(73) Assignee: GlaxoSmithKline istraživački Centar Zagreb d.o.o., Zagreb (HR)

( * ) Notice: Subject to any disclaimer, the term of this patent is extended or adjusted under 35 U.S.C. 154(b) by 0 days.

(21) Appl. No.: 10/515,679

(22) PCT Filed: May 20, 2003

(86) PCT No.: PCT/HR03/00026

§ 371 (c)(1),
(2), (4) Date: May 24, 2005

(87) PCT Pub. No.: WO03/097648

PCT Pub. Date: Nov. 27, 2003

(65) Prior Publication Data

US 2005/0209191 A1    Sep. 22, 2005

(30) Foreign Application Priority Data

May 21, 2002    (HR) .......................... P 20020440 A

(51) Int. Cl.
| | | |
|---|---|---|
| A61K 31/407 | (2006.01) | |
| A61K 31/38 | (2006.01) | |
| A61K 31/335 | (2006.01) | |
| C07D 491/044 | (2006.01) | |
| C07D 337/14 | (2006.01) | |
| C07D 313/14 | (2006.01) | |

(52) U.S. Cl. .................. 514/63; 514/410; 514/431; 514/450; 548/406; 548/421; 549/4; 549/12; 549/214; 549/354

(58) Field of Classification Search .................. 514/63, 514/410, 431, 450; 548/406, 421; 549/4, 549/12, 214, 354
See application file for complete search history.

(56) References Cited

U.S. PATENT DOCUMENTS

| | | |
|---|---|---|
| 3,711,489 A | 1/1973 | Lombardino |
| 3,773,940 A | 11/1973 | Schindler et al. |
| 3,781,294 A | 12/1973 | Lombardino |
| 3,859,439 A | 1/1975 | Blattner et al. |
| 4,112,110 A | 9/1978 | Blattner |
| 4,198,421 A | 4/1980 | Cherkofsky et al. |
| 4,267,184 A | 5/1981 | Cherkofsky |
| 4,267,190 A | 5/1981 | Cherkofsky |
| 4,271,179 A | 6/1981 | van der Burg |
| 2005/0148578 A1* | 7/2005 | Mercep et al. .............. 514/215 |

FOREIGN PATENT DOCUMENTS

| | | |
|---|---|---|
| CA | 967573 | 5/1975 |
| EP | 0 125 484 | 11/1984 |
| EP | 0 357 126 | 3/1990 |
| EP | 0 372 445 | 6/1990 |
| HR | 20000310 | 2/2002 |
| WO | WO-91/18885 | 12/1991 |
| WO | WO-98/54186 | 12/1998 |
| WO | WO-01/87890 | 11/2001 |
| WO | WO-03/097648 | 11/2003 |

OTHER PUBLICATIONS

Novacek et al. "Reaction of 8-chloro-10-phenylhydrazono-10, 11-dihydro-dibenzo[b,f]thepine with aromatic aldehydes" Collection Czechoslov. Chem. Commun. 1976, vol. 41, pp. 785-787.*

Wermuth et al., "Molecular Variations Based on Isosteric Replacements," Practice of Medicinal Chemistry, 1996, pp. 203-237.

Olivera et al., Dibenzoxepino '4,5-d pyrazoles: a facile approach via the Ullman-ether reaction, Tetrahedron Letters, 2000, 41(22):4353-4360.

Schulz et al, Synthese von 1,3a,3,12b-Tetrahydro-dibenzo[b,f]-pyrazolo[3,4-d]azepin-Derivaten, Z. Chem. 1988, 28:181-182.

Funke et al., Physico-chemical Properties and Stability of trans-5-Chloro-2-methyl-2,3,3a,12b-tetrahydro-1h-dibenz[2,3:6,7]oxepino[4,5-c]pyrrolidine Maleate, Arzeim-Forsch., 1190, 40:536-539.

Bennett et al., Reaction of 5-Acetyl-10, didehydro-5H-dibenz[b,f] azepine with Pyrrole, N-Methylpyrrole, Imadazole and N-Methylimidazole: Cycloaddition Versus Michael Addition,J. Heterocycl. Chem., 1994, 31:293-296.

Georgopoulos et al., Transmembrane TNF Is Sufficient To Induce Localized Tissue Toxicity and Chronic Inflammatory Arthritis In Transgenic Mice, J. Inflamm., 1996, 46:86-97.

Dinarello, Interleukin-1, Rev. Infect Disease, 1984, 6(1):51-95.

Dinarello, An Update on Human Interleukin-1: From Molecular Biology to Clinical Relevance, J. Clinical Immunology, 1985, 5:287.

Pfeffer et al., Mice Deficient for the 55kd Tumor Necrosis Factor Receptor Are Resistant to Endotixic Shock, yet Succumb to L. monocytogenes Infection, Cell, 1993, 73:457-467.

(Continued)

*Primary Examiner*—Kamal A. Saeed
*Assistant Examiner*—Joseph R. Kosack
(74) *Attorney, Agent, or Firm*—J. Scott Young

(57) ABSTRACT

The present invention relates to 1-aza-dibenzoazulene derivatives, to their pharmacologically acceptable salts and solvates, to processes and intermediates for the preparation thereof as well as to their antiinflammatory effects, especially to the inhibition of tumour necrosis factor-α (TNF-α) production and the inhibition of interleukin-1 (IL-1) production as well as to their analgetic action.

12 Claims, No Drawings

OTHER PUBLICATIONS

Mori et al., Attenuation of Collagen-Induced Arthritis in 55-kDa TNF Receptor Type 1 (TNFR1)-IgG1-Treated and TNFR1-Deficient Mice, J. Immunol., 1996, 157:3178-3182.

Carswell et al., An endotoxin-induced serum factor that causes necrosis of tumors, Proc. Natl. Acad. Sci. U.S.A., 1975, 72:3666-3670.

Bresnihan, Treatment with Recombinant Human Interleukin-1 Receptor Antagonist (rhIL-1ra) in Rheumatoid Arthritis (RA); Results of a Randomized Double-Blind, Placebo-Controlled Multicenter trial, Arthrit. Rheum., 1996, 39:73.

Van Assche and Rutgeerts, Anti-TNF agents in Crohn's disease, Exp. Opin. Invest. Drugs, 2000, 9:103-111.

Elliott et al., Randmoised double-blind comparison of chimeric monoclonal antibody to tumor necrosis factor alpha (cA2) versus placebo in rheumatoid arthritis, The Lancet, 1994, 344:1105-1110.

Mattioli and Ghia, omega-Dialkylaminoalkyl Ethers of Phenyl-(5-substituted 1-phenyl-1H-pyrazol-4-yl)methanols with Analgesic and Anti-inflammatory Activity, J. Heterocyclic Chem., 1997, 34:963-968, Collier et al., The Abdominal Constriction Response and Its Suppression By Analgesic Drugs in the Mouse, Br. J. Pharmac. Chemother., 1968, 32-295-310.

Schweizer et al., Combined automated writhing/motility test for testing analgesics, Agents and Actions, 1988, 23:29-31.

Fukawa et al., A Method for Evaluating Analgesic Agents in Rats, J. Pharmacol. Meth., 1980, 4:251-259.

Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, J. Pharmac. Env. Therap., 1996, 279(3): 1453-1461.

Keffer et al., Transgenic mice expressing human tumour necrosis factor: a predictive genetic model of arthritis, EMBO, J., 1991, 10:4025-4031.

* cited by examiner

1-AZA-DIBENZOAZULENES AS INHIBITORS OF TUMOUR NECROSIS FACTOR PRODUCTION AND INTERMEDIATES FOR THE PREPARATION THEREOF

This application is a National Stage under 35 U.S.C. §371 of PCT International Application No. PCT/HR03/00026, filed May 20, 2003, which claims the benefit under 35 U.S.C. §119(e) of prior Croatian Application No. P20020440A, filed May 21, 2002, the entire contents of which are incorporated herein by reference.

TECHNICAL FIELD

The present invention relates to 1-aza-dibenzoazulene derivatives, to their pharmacologically acceptable salts and solvates, to processes and intermediates for the preparation thereof as well as to their antiinflammatory effects, especially to the inhibition of tumour necrosis factor-$\alpha$ (TNF-$\alpha$) production and the inhibition of interleukin-1 (IL-1) production as well as to their analgetic action.

PRIOR ART

There are numerous literature data relating to various aza- and diaza-dibenzoazulenes and to the preparation thereof. It is well-known that some compounds of such structure and salts thereof have an antiinflammatory action and represent a novel class of compounds having such an action. Thus in a series of patents (U.S. Pat. No. 3,711,489, U.S. Pat. No. 3,781,294 and CA 967,573) the preparation of dibenzoazulenes of imidazole class with various 2-substituents such as trifluoromethyl, pyridyl, naphthyl, phenyl and substituted phenyl is disclosed. There were also prepared corresponding imidazole derivatives with 2-alkylthio substituents of similar action (U.S. Pat. No. 4,198,421; EP 372,445 and WO 9,118,885).

Dibenzoazulenes of pyrazole class having alkyl, phenyl or substituted phenyl (FR 2,504,140; and Olivera R et al., *Tetrahedron Lett.*, 2000, 41:4353–4356 and 4357–4360) or acetyl and ethoxycarbonyl (Schulz H J et al., *Z. Chem.*, 1988, 28:181–182) in 2-position are known as well.

There are also literature data disclosing the preparation of 2-aza-dibenzoazulene derivatives such as N-methyl derivatives (Funke C et al., *Arzneim-Forsch.*, 1990, 40:536–539; Bennett R A et al., *J. Heterocycl. Chem.*, 1994, 31:293–296) and several patents disclosing dihydro derivatives of 2-aza-dibenzoazulenes (U.S. Pat. No. 3,773,940; U.S. Pat. No. 3,859,439; U.S. Pat. No. 4,112,110; EP 125,484) and tetrahydro derivatives of 2-aza-dibenzoazulenes (U.S. Pat. No. 4,271,179; EP 357,126 and WO 9,854,186). Further, also aromatic 1-thia-dibenzoazulenes having aminoalkyloxy substituents on thiophene ring, which also possess an antiinflammatory action (WO 01/87890) are known.

According to our knowledge and to available literature data, completely unsaturated aromatic 1-aza-dibenzoazulenes of the present invention have hitherto not been prepared or disclosed. Nor is it known that such compounds could possess an antiinflammatory action (inhibitors of TNF-$\alpha$ production, inhibitors of IL-1 production) or an analgetic action, said actions also being an object of the present invention. In 1975 TNF-$\alpha$ was defined as a serum factor induced by endotoxin and causing tumour necrosis in vitro and in vivo (Carswell E A et al., *Proc. Natl. Acad. Sci. U.S.A.*, 1975, 72:3666–3670). Besides an antitumour action, TNF-$\alpha$ also possesses numerous other biological actions important in the homeostasis of organisms and in pathophysiological conditions. The main sources of TNF-$\alpha$ are monocytes-macrophages, T-lymphocytes and mastocytes.

The discovery that anti-TNF-$\alpha$ antibodies (cA2) are effective in treating patients with rheumatoid arthritis (RA) (Elliott M et al., *Lancet*, 1994, 344:1105–1110) led to an increased interest in finding novel TNF-$\alpha$ inhibitors as possible potent drugs for RA. Rheumatoid arthritis is an autoimmune chronic inflammatory disease characterized by irreversible pathological changes in the joints. In addition to RA, TNF-$\alpha$ antagonists may also be used in numerous pathological conditions and diseases such as spondylitis, osteoarthritis, gout and other arthritic conditions, sepsis, septic shock, toxic shock syndrom, atopic dermatitis, contact dermatitis, psoriasis, glomerulonephritis, lupus erythematosus, scleroderma, asthma, cachexia, chronic obstructive lung disease, congestive cardiac arrest, insulin resistance, lung fibrosis, multiple sclerosis, Crohn's disease, ulcerative colitis, viral infections and AIDS.

Some of the proofs indicating the biological importance of TNF-$\alpha$ were obtained by in vivo experiments in mice, in which mouse genes for TNF-$\alpha$ or its receptor were inactivated. Such animals are resistant to collagen-induced arthritis (Mori L et al., *J. Immunol.*, 1996, 157:3178–3182) and to endotoxin-caused shock (Pfeffer K et al., *Cell*, 1993, 73:457–467). In animal assays where the TNF-$\alpha$ level was increased, a chronic inflammatory polyarthritis occurred (Georgopoulos S et al., *J. Inflamm.*, 1996, 46:86–97; Keffer J et al., *EMBO J.*, 1991, 10:4025–4031) and its pathological picture was alleviated by inhibitors of TNF-$\alpha$ production. The treatment of such inflammatory and pathological conditions usually includes the application of non-steroid antiinflammatory drugs and, in more severe cases, gold salts, D-penicillinamine or methotrexate are administered. Said drugs act symptomatically, but they do not stop the pathological process. Novel approaches in the therapy of rheumatoid arthritis are based upon drugs such as tenidap, leflunomide, cyclosporin, FK-506 and upon biomolecules neutralizing the TNF-$\alpha$ action. At present there are commercially available etanercept (Enbrel, Immunex/Wyeth), a fusion protein of the soluble TNF-$\alpha$ receptor, and infliximab (Remicade, Centocor), a chimeric monoclonal human and mouse antibody. Besides in RA therapy, etanercept and infliximab are also registered for the therapy of Crohn's disease (*Exp. Opin. Invest. Drugs*, 2000, 9:103).

In an optimum RA therapy, besides inhibition of TNF-$\alpha$ secretion, also the inhibition of IL-1 secretion is very important since IL-1 is an important cytokin in cell regulation and immunoregulation as well as in pathophysiological conditions such as inflammation (Dinarello C A et al., *Rev. Infect. Disease*, 1984, 6:51). Well-known biological activities of IL-1 are: activation of T-cells, induction of elevated temperature, stimulation of the secretion of prostaglandine or collagenase, chemotaxia of neutrophils and reduction of iron level in plasma (Dinarello C A, *J. Clinical Immunology*, 1985, 5:287). Two receptors to which IL-1 may bind are well-known: IL-1RI and IL-1RII. Whereas IL-1RI transfers a signal intracellularly, IL-1RII is situated on the cell surface and does not transfer a signal inside the cell. Since IL-1-RII binds IL-1 as well as IL-1-RI, it may act as a negative regulator of IL-1 action. Besides this mechanism of signal transfer regulation in cells, another natural antagonist of IL-1 receptor (IL-1ra) is present in cells. This protein binds to IL-1RI but does not cause its stimulation. Its potency in stopping the transfer of IL-1 stimulated signal is not high and its concentration has to be 500 times higher than that of IL-1 in order to achieve a break in the signal transfer. Recombinant human IL-1ra (Amgen) was clinically tested (Bresnihan B et al., *Arthrit. Rheum.*, 1996, 39:73) and the obtained results indicated an improvement of the clinical picture over a placebo in RA patients. These results indicate the importance of the inhibition of IL-1 action in treating diseases such as RA where IL-1 production is disturbed. Since there exists a synergistic action of TNF-α and IL-1, dual TNF-α and IL-1 inhibitors may be used in treating conditions and diseases related to an enhanced secretion of TNF-α and IL-1.

Inventive Solution

The present invention relates to 1-aza-dibenzoazulene compounds of the formula I:

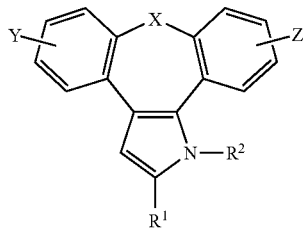

I wherein

X may be $CH_2$ or a hetero atom such as O, S, S(=O), S(=O)$_2$, or $NR^a$, wherein $R^a$ is hydrogen or a protecting group;

Y and Z independently from each other denote hydrogen, one or more identical or different substituents linked to any available carbon atom, and may be halogen, $C_1$–$C_4$ alkyl, $C_2$–$C_4$ alkenyl, $C_2$–$C_4$ alkinyl, halo-$C_1$–$C_4$ alkyl, hydroxy, $C_1$–$C_4$ alkoxy, trifluoromethoxy, $C_1$–$C_4$ alkanoyl, amino, amino-$C_1$–$C_4$ alkyl, $C_1$–$C_4$ alkylamino, N-($C_1$–$C_4$-alkyl)amino, N,N-di($C_1$–$C_4$-alkyl)amino, thiol, $C_1$–$C_4$ alkylthio, sulfonyl, $C_1$–$C_4$ alkylsulfonyl, sulfinyl, $C_1$–$C_4$ alkylsulfinyl, carboxy, $C_1$–$C_4$ alkoxycarbonyl, cyano, nitro;

$R^1$ may be hydrogen, halogen, an optionally substituted $C_1$–$C_7$ alkyl or $C_2$–$C_7$ alkenyl, $C_2$–$C_7$ alkinyl, an optionally substituted aryl or heteroaryl and a heterocycle, hydroxy, hydroxy-$C_2$–$C_7$ alkenyl, hydroxy-$C_2$–$C_7$ alkinyl, $C_1$–$C_7$ alkoxy, thiol, thio-$C_2$–$C_7$ alkenyl, thio-$C_2$–$C_7$ alkinyl, $C_1$–$C_7$ alkylthio, amino, N-($C_1$–$C_7$)alkylamino, N,N-di($C_1$–$C_7$-alkyl)amino, ($C_1$–$C_7$-alkyl)amino, amino-$C_2$–$C_7$ alkenyl, amino-$C_2$–$C_7$ alkinyl, amino-$C_1$–$C_7$ alkoxy, $C_1$–$C_7$ alkanoyl, aroyl, oxo-$C_1$–$C_7$ alkyl, $C_1$–$C_7$ alkanoyloxy, carboxy, an optionally substituted $C_1$–$C_7$ alkyloxycarbonyl or aryloxycarbonyl, carbamoyl, N-($C_1$–$C_7$-alkyl)carbamoyl, N,N-di($C_1$–$C_7$-alkyl)carbamoyl, cyano, cyano-$C_1$–$C_7$ alkyl, sulfonyl, $C_1$–$C_7$ alkylsulfonyl, sulfinyl, $C_1$–$C_7$ alkylsulfinyl, nitro, or a substituent of the formula A:

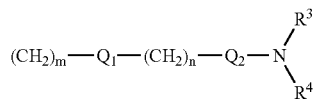

A wherein $R^3$ and $R^4$ simultaneously or independently from each other may be hydrogen, $C_1$–$C_4$ alkyl, aryl or together with N have the meaning of an optionally substituted heterocycle or heteroaryl;

m and n represent an integer from 0 to 3;

$Q_1$ and $Q_2$ represent, independently from each other, oxygen, sulfur or groups:

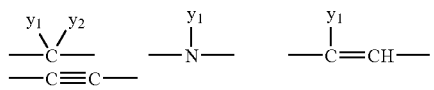

wherein the substituents $y_1$ and $y_2$ independently from each other may be hydrogen, halogen, an optionally substituted $C_1$–$C_4$ alkyl or aryl, hydroxy, $C_1$–$C_4$ alkoxy, $C_1$–$C_4$ alkanoyl, thiol, $C_1$–$C_4$ alkylthio, sulfonyl, $C_1$–$C_4$ alkylsulfonyl, sulfinyl, $C_1$–$C_4$ alkylsulfinyl, cyano, nitro or together form carbonyl or imino group;

$R^2$ has the meaning of hydrogen, optionally substituted $C_1$–$C_7$ alkyl or aryl or a protecting group: formyl, $C_1$–$C_7$ alkanoyl, $C_1$–$C_7$ alkoxycarbonyl, arylalkyloxycarbonyl, aroyl, arylalkyl, $C_1$–$C_7$ alkylsilyl;

as well as to pharmacologically acceptable salts and solvates thereof.

The term "halo", "hal" or "halogen" relates to a halogen atom which may be fluorine, chlorine, bromine or iodine.

The term "alkyl" relates to alkyl groups with the meaning of alkanes wherefrom radicals are derived, which radicals may be straight, branched or cyclic or a combination of straight and cyclic ones as well as of branched and cyclic ones. The preferred straight or branched alkyls are e.g. methyl, ethyl, propyl, isopropyl, butyl, sec-butyl and tert-butyl. The preferred cyclic alkyls are e.g. cyclopentyl or cyclohexyl.

The term "haloalkyl" relates to alkyl groups which must be substituted with at least one halogen atom. The most frequent haloalkyls are e.g. chloromethyl, dichloromethyl, trifluoromethyl or 1,2-dichloropropyl.

The term "alkenyl" relates to alkenyl groups having the meaning of hydrocarbon radicals, which may be straight, branched or cyclic or are a combination of straight and cyclic ones or branched and cyclic ones, but having at least one carbon-carbon double bond. The most frequent alkenyls are ethenyl, propenyl, butenyl or cyclohexenyl.

The term "alkinyl" relates to alkinyl groups having the meaning of hydrocarbon radicals, which are straight or branched and contain at least one and at most two carbon-carbon triple bonds. The most frequent alkinyls are e.g. ethinyl, propinyl or butinyl.

The term "alkoxy" relates to straight or branched chains of alkoxy group. Examples of such groups are methoxy, propoxy, prop-2-oxy, butoxy, but-2-oxy or methylprop-2-oxy.

The term "aryl" relates to groups having the meaning of an aromatic ring, e.g. phenyl, as well as to fused aromatic rings. Aryl contains one ring with at least 6 carbon atoms or two rings with totally 10 carbon atoms and with alternating double (resonant) bonds between carbon atoms. The most freqently used aryls are e.g. phenyl or naphthyl. In general, aryl groups may be linked to the rest of the molecule by any available carbon atom via a direct bond or via a $C_1$–$C_4$ alkylene group such as methylene or ethylene.

The term "heteroaryl" relates to groups having the meaning of aromatic and partially aromatic groups of a monocyclic or bicyclic ring with 4 to 12 atoms, at least one of them being a hetero atom such as O, S or N, and the available nitrogen atom or carbon atom is the binding site of the group to the rest of the molecule either via a direct bond or via a $C_1$–$C_4$ alkylene group defined earlier. Examples of this type are thiophenyl, pyrrolyl, imidazolyl, pyridinyl, oxazolyl, thiazolyl, pyrazolyl, tetrazolyl, pirimidinyl, pyrazinyl, quinolinyl or triazinyl.

The term "heterocycle" relates to five-member or six-member, fully saturated or partly unsaturated heterocyclic groups containing at least one hetero atom such as O, S or N, and the available nitrogen atom or carbon atom is the binding site of the group to the rest of the molecule either via a direct bond or via a $C_1$–$C_4$ alkylene group defined earlier. The most frequent examples are morpholinyl, piperidyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The term "optionally substituted" alkyl relates to alkyl groups, which may be optionally additionally substituted with one, two, three or more substituents. Such substituents may be a halogen atom (preferably fluorine or chlorine), hydroxy, $C_1$–$C_4$ alkoxy (preferably methoxy or ethoxy), thiol, $C_1$–$C_4$ alkylthio (preferably methylthio or ethylthio), amino, N-($C_1$–$C_4$) alkylamino (preferably N-methylamino or N-ethylamino), N,N-di($C_1$–$C_4$-alkyl)-amino (preferably dimethylamino or diethylamino), sulfonyl, $C_1$–$C_4$ alkylsulfonyl (preferably methylsulfonyl or ethylsulfonyl), sulfinyl, $C_1$–$C_4$ alkylsulfinyl (preferably methylsulfinyl).

The term "optionally substituted" alkenyl relates to alkenyl groups optionally additionally substituted with one, two or three halogen atoms. Such substituents may be e.g. 2-chloroethenyl, 1,2-dichloroethenyl or 2-bromo-propene-1-yl.

The term "optionally substituted" aryl, heteroaryl or heterocycle relates to aryl, heteroaryl or heterocyclic groups which may be optionally additionally substituted with one or two substituents. The substituents may be halogen (preferably chlorine or fluorine), $C_1$–$C_4$ alkyl (preferably methyl, ethyl or isopropyl), cyano, nitro, hydroxy, $C_1$–$C_4$ alkoxy (preferably methoxy or ethoxy), thiol, $C_1$–$C_4$ alkylthio (preferably methylthio or ethylthio), amino, N-($C_1$–$C_4$) alkylamino (preferably N-methylamino or N-ethylamino), N,N-di($C_1$–$C_4$-alkyl)-amino (preferably N,N-dimethylamino or N,N-diethylamino), sulfonyl, $C_1$–$C_4$ alkylsulfonyl (preferably methylsulfonyl or ethylsulfonyl), sulfinyl, $C_1$–$C_4$ alkylsulfinyl (preferably methylsulfinyl).

When X has the meaning of $NR^a$ and $R^a$ has the meaning of a protecting group, $R^a$ relates to groups such as alkyl (preferably methyl or ethyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).

When $R^3$ and $R^4$ together with N have the meaning of heteroaryl or heterocycle, this means that such heteroaryls or heterocycles have at least one carbon atom replaced by a nitrogen atom, through which the groups are linked to the rest of the molecule. Examples of such groups are morpholine-4-yl, piperidine-1-yl, pyrrolidine-1-yl, imidazole-1-yl or piperazine-1-yl.

The term "pharmaceutically suitable salts" relates to salts of the compounds of the formula I and include e.g. salts with $C_1$–$C_4$ alkylhalides (preferably methyl bromide, methyl chloride) (quaternary ammonium salts), with inorganic acids (hydrochloric, hydrobromic, phosphoric, metaphosphoric, nitric or sulfuric acids) or with organic acids (tartaric, acetic, citric, maleic, lactic, fumaric, benzoic, succinic, methane sulfonic or p-toluene sulfonic acids).

Some compounds of the formula I may form salts with organic or inorganic acids or bases and these are also included in the present invention.

Solvates (most frequently hydrates), which may be formed by compounds of the formula I or salts thereof, are also an object of the present invention.

Depending upon the nature of particular substituents, the compounds of the formula I may have geometric isomers and one or more chiral centres so that there can exist enantiomers or diastereoisomers. The present invention also relates to such isomers and mixtures thereof including racemates.

The present invention also relates to all possible tautomeric forms of particular compounds of the formula I.

A further object of the present invention relates to the preparation of compounds of the formula I according to processes comprising a) for compounds of the formula I, wherein $R^1$ is hydrogen, a cyclization of compounds of the formula III:

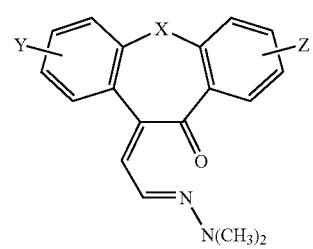

III b) for compounds of the formula I, wherein $Q_1$ has the meaning of —O—, a reaction of alcohols of the formula IV:

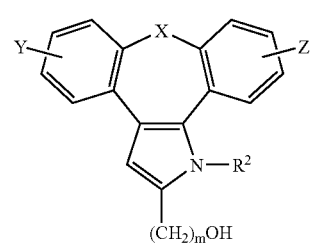

IV with compounds of the formula V:

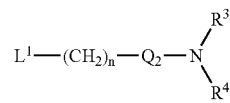

V wherein $L^1$ has the meaning of a leaving group, c) for compounds of the formula I, wherein $Q_1$ has the meaning of —O—, —NH—, —S— or —C≡C—, a reaction of compounds of the formula IVa:

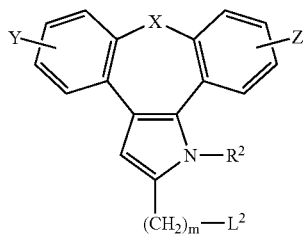

IVa wherein $L^2$ has the meaning of a leaving group, with compounds of the formula Va:

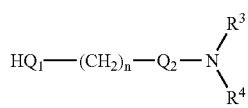

Va d) for compounds wherein $Q_1$ has the meaning of —O—, —NH— or —S—, a reaction of compounds of the formula IVb:

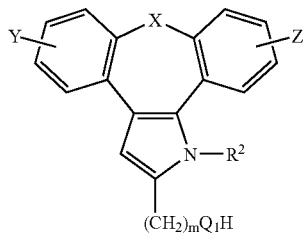

IVb with compounds of the formula V, wherein $L^1$ has the meaning of a leaving group, e) for compounds wherein $Q_1$ has a meaning of —C≡C—, a reaction of compounds of the formule IVb, wherein $Q_1$ has the meaning of carbonyl, with phosphorous ylides.

Preparation methods:

a) Compounds of the formula I, wherein $R^1$ has the meaning of hydrogen, are obtained by reaction of the compounds of the formula III with $Na_2S_2O_4$ or $Na_2SO_3$; in an aqueous-alcoholic medium (preferably ethanol-water) under heating (preferably at boiling temperature) for 1 to 5 hours (U.S. Pat. No. 4,267,190). The obtained crude product may be purified by recrystallization or column chromatography.

The starting compounds for preparing compounds of the formula III are the corresponding dibenzo-cycloheptanones of the formula IIIa:

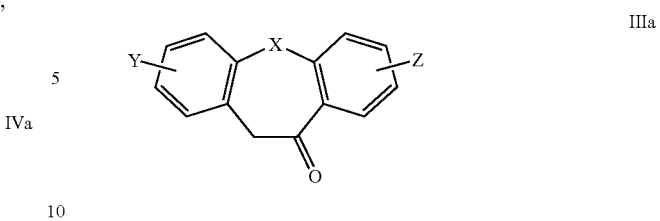

IIIa and a compound of the formula IIIb:

IIIb

The compounds of the formula IIIa and the compound of the formula IIIb are already known or are prepared by methods disclosed for the preparation of analogous compounds.

Compounds of the formula III may be prepared in an alcoholic medium in the presence of a corresponding alcoholate (preferably sodium ethoxide in ethanol) at elevated temperature (50° C. to 100° C.) during 1 to 5 hours (Severin T, Poehlmann H, *Chem. Ber.* 1977, 110:491–499). Products consisting of a mixture of geometric isomers may be isolated and purified by chromatography on silica gel column or may be converted to corresponding pyrrol derivatives without isolation by cyclization.

b) Compounds of the formula I according to the present process may be prepared by reaction of alcohols of the formula IV and compounds of the formula V, wherein $L^1$ has the meaning of a leaving group, which may be a halogen atom (most frequently bromine, iodine or chlorine) or sulfonyloxy group (most frequently trifluoromethylsulfonyloxy or p-toluenesulfonyloxy). The reaction of condensation may be carried out according to methods disclosed for the preparation of analogous compounds (Menozzi G et al., *J. Heterocyclic Chem.*, 1997, 34:963–968 or WO 01/87890). The reaction is carried out at a temperature from 20° C. to 100° C. during 1 to 24 hours in a two-phase system (preferably with 50% NaOH/toluene) in the presence of a phase transfer catalyst (preferably benzyl triethyl ammonium chloride, benzyl triethyl ammonium bromide, cetyl trimethyl bromide). After treating the reaction mixture, the products formed are isolated by recrystallization or chromatography on a silica gel column.

The starting substances, alcohols of the formula IV, may be prepared from the compounds of the formula I, wherein $R^1$ has the meaning of a suitable functional group and $R^2$ has the meaning of a protecting group. Thus e.g. alcohols of the formula IV may be obtained by the reduction of aldehyde, carboxyl of alkyloxycarbonyl group (e.g. methyloxycarbonyl or ethyloxycarbonyl) by using metal hydrides such as lithium aluminum hydride or sodium borohydride. Further, alcohols of the formula IV may be prepared by hydrolysis of the corresponding esters in an alkaline or acidic medium.

The starting compounds of the formula V are already known or are prepared according to methods disclosed for the preparation of analogous compounds.

c) Compounds of the formula I according to the present process may be prepared by reacting compounds of the formula IVa, wherein $L^2$ has the meaning of a leaving group defined earlier for $L^1$, and compounds of the formula Va, wherein $Q_1$ has the meaning of oxygen, nitrogen, sulfur or —C≡C—. The most suitable condensation reactions are reactions of nucleophilic substitution on a saturated carbon atom as disclosed in the literature.

The starting compounds of the formula IVa (most frequently halogens) may be obtained by halogenation (e.g. bromination of chlorination) of the compounds of the formula IV with common halogenating agents (hydrobromic acid, $PBr_3$, $SOCl_2$ or $PCl_5$) by processes disclosed in the literature. The obtained compounds may be isolated or may be used without isolation as appropriate intermediates for the preparation of the compounds of the formula I.

The starting compounds of the formula Va are already known or are prepared according to methods disclosed for the preparation of analogous compounds.

d) The compounds of the formula I, wherein $Q_1$ has the meaning of —O—, —NH— or —S—, may be prepared by condensation of the compounds of the formula IVb and of compounds of the formula V, wherein $L^1$ has the meaning of a leaving group defined earlier. The reaction may be carried out as disclosed in method b) or at reaction conditions for a nucleophilic substitution disclosed in the literature. The starting alcohols, amines and thiols may be obtained by a reaction of water, ammonia or hydrogen sulfide with compounds IVa according to processes disclosed in the literature.

e) The alcohols of the structure IV may be oxidized to corresponding compounds of the formula IVb, wherein $Q_1$ has the meaning of carbonyl, which may further, by reaction with corresponding ylide reagents, result in a prolongation of the chain and in the formation of an alkenyl substituent with carbonyl or ester groups as disclosed in HR patent application No. 20000310.

Besides the reactions mentioned above, the compounds of the formula I may be prepared by transforming other compounds of the formula I and it is to be understood that the present invention also comprises such compounds and processes. A special example of a change of a functional group is the reaction of the aldehyde group with chosen phosphorous ylides resulting in a prolongation of the chain and the formation of an alkenyl substituent with carbonyl or ester groups as disclosed in HR patent application No. 20000310. These reactions are carried out in solvents such as benzene, toluene or hexane at elevated temperature (most frequently at boiling temperature).

By reacting the compounds of the formula IVa with 1-alkyne in an alkaline medium (such as sodium amide in ammonia), the compounds of the formula I, wherein $Q_1$ is —C≡C—, are obtained. The reaction conditions of this process are disclosed in the literature. At similar reaction conditions (nucleophilic substitution) various ether, thioether or amine derivatives may be prepared.

The formylation of the compounds of the formula I by processes such as e.g. Vilsmeier acylation (U.S. Pat. No. 4,267,184) or reaction of n-BuLi and NAN-dimethylformamide is a further general example of a transformation. The reaction conditions of these processes are well-known in the literature.

By hydrolysis of the compounds of the formula I having nitrile, amide or ester groups, there may be prepared compounds with a carboxyl group, which are suitable intermediates for the preparation of other compounds with novel functional groups such as e.g. esters, amides, halides, anhydrides, alcohols or amines.

Oxidation or reduction reactions are a further possibility of the change of substituents in the compounds of the formula I. Most frequently used oxidation agents are peroxides (hydrogen peroxide, m-chloroperbenzoic acid or benzoyl peroxide) or permanganate, chromate or perchlorate ions. Thus e.g. by the oxidation of an alcohol group by pyridinyl dichromate or pyridinyl chlorochromate, an aldehyde group is formed, which group may be converted to a carboxyl group by further oxidation.

By a selective oxidation of alkylthio group, alkylsulfinyl or alkylsulfonyl groups may be prepared.

By the reduction of the compounds with a nitro group, the preparation of amino compounds is made possible. The reaction is carried out under usual conditions of catalytic hydrogenation or electrochemically. By catalytic hydrogenation using palladium on carbon, alkenyl substituents may be converted to alkyl ones or nitrile group can be converted to aminoalkyl.

Various substituents of the aromatic structure in the compounds of the formula I may be introduced by standard substitution reactions or by usual changes of individual functional groups. Examples of such reactions are aromatic substitutions, alkylations, halogenation, hydroxylation as well as oxidation or reduction of substituents. Reagents and reaction conditions are known from the literature. Thus e.g. by aromatic substitution a nitro group is introduced in the presence of concentrated nitric acid and sulfuric acid. By using acyl halides or alkyl halides, the introduction of an acyl group or an alkyl group is made possible. The reaction is carried out in the presence of Lewis acids such as aluminum- or iron-trichloride in conditions of Friedel-Crafts reaction. By the reduction of the nitro group, an amino group is obtained, which is by the reaction of diazotizing converted to a suitable starting group, which may be replaced with one of the following groups: H, CN, OH, Hal.

In order to prevent undesired interaction in chemical reactions, it is often necessary to protect certain groups such as e.g. hydroxy, amino, thio or carboxy. For this purpose a great number of protecting groups may be used (Green TW, Wuts PGH, Protective Groups in Organic Synthesis, John Wiley and Sons, 1999) and the choice, use and elimination thereof are conventional methods in chemical synthesis.

A convenient protection for amino or alkylamino groups are groups such as e.g. alkanoyl (acetyl), alkoxycarbonyl (methoxycarbonyl, ethoxycarbonyl or tert-butoxycarbonyl); arylmethoxycarbonyl (benzyloxycarbonyl), aroyl (benzoyl) or alkylsilyl (trimethylsilyl or trimethylsilylethoxymethyl) groups. The conditions of removing a protecting group depend upon the choice and the characteristics of this group. Thus e.g. acyl groups such as alkanoyl, alkoxycarbonyl or aroyl may be eliminated by hydrolysis in the presence of a base (sodium hydroxide or potassium hydroxide), tert-butoxycarbonyl or alkylsilyl (trimethylsilyl) may be eliminated by treatment with a suitable acid (hydrochloric, sulfuric, phosphoric or trifluoroacetic acid), whereas arylmethoxycarbonyl group (benzyloxycarbonyl) may be eliminated by hydrogenation using a catalyst such as palladium on carbon.

Salts of the compounds of the formula I may be prepared by generally known processes such as e.g. by reacting the compounds of the formula I with a corresponding base or acid in an appropriate solvent or solvent mixture e.g. ethers (diethylether) or alcohols (ethanol, propanol or isopropanol).

Another object of the present invention concerns the use of the present compounds in the therapy of inflammatory diseases and conditions, especially all diseases and conditions induced by excessive TNF-α and IL-1 secretion.

Inhibitors of production of cytokins or inflammation mediators, which are the object of the present invention, or pharmacologically acceptable salts thereof may be used in production of drugs for the treatment and prophylaxis of any pathological condition or disease induced by excessive unregulated production of cytokins or inflammation mediators, which drugs should contain an effective dose of said inhibitors.

The present invention specifically relates to an effective dose of TNF-α inhibitor, which may be determined by usual methods.

Further, the present invention relates to a pharmaceutical formulation containing an effective non-toxic dosis of the present compounds as well as pharmaceutically acceptable carriers or solvents.

The preparation of pharmaceutical formulations may include blending, granulating, tabletting and dissolving ingredients. Chemical carriers may be solid or liquid. Solid carriers may be lactose, sucrose, talcum, gelatine, agar, pectin, magnesium stearate, fatty acids etc. Liquid carriers may be syrups, oils such as olive oil, sunflower oil or soya bean oil, water etc. Similarly, the carrier may also contain a component for a sustained release of the active component such as e.g. glyceryl monostearate or glyceryl distearate. Various forms of pharmaceutical formulations may be used. Thus, if a solid carrier is used, these forms may be tablets, hard gelatine capsules, powder or granules, which may be administered in capsules per os. The amount of the solid carrier may vary, but it is mainly from 25 mg to 1 g. If a liquid carrier is used, the formulation would be in the form of a syrup, emulsion, soft gelatine capsules, sterile injectable liquids such as ampoules or non-aqueous liquid suspensions.

Compounds according to the present invention may be applied per os, parenterally, locally, intranasally, intrarectally and intravaginally. The parenteral route herein means intravenous, intramuscular and subcutaneous applications. Appropriate formulations of the present compounds may be used in the prophylaxis as well as in the treatment of inflammatory diseases and conditions induced by an excessive unregulated production of cytokins or inflammation mediators, primarily TNF-α. They comprise e.g. rheumatoid arthritis, rheumatoid spondylitis, osteoarthritis and other arthritic pathological conditions and diseases, eczemas, psoriasis and other inflammatory skin conditions, inflammatory eye diseases, Crohn's disease, ulcerative colitis and asthma.

The inhibitory action of the present compounds upon TNF-α and IL-1 secretion was determined by the following in vitro and in vivo experiments:

Determination of TNF-α and IL-1 Secretion in Human Peripheral Blood Mononuclear Cells in vitro Human peripheral blood mononuclear cells (PBMC) were prepared from heparinized whole blood after separating PBMC on Ficoll-Paque™ Plus (Amersham-Pharmacia). To determine the TNF-α level, $3.5–5 \times 10^4$ cells were cultivated in a total volume of 200 μl for 18 to 24 hours on microtitre plates with a flat bottom (96 wells, Falcon) in RPMI 1640 medium, into which there were added 10% FBS (Fetal Bovine Serum, Biowhittaker) previously inactivated at 56° C./30 min, 100 units/ml of penicillin, 100 mg/ml of streptomycin and 20 mM HEPES (GIBCO). The cells were incubated at 37° C. in an atmosphere with 5% $CO_2$ and 90% humidity. In a negative control the cells were cultivated only in the medium (NC), whereas in a positive control TNF-α secretion was triggered by adding 1 ng/ml of lipopolysaccharides (LPS, E. coli serotype 0111:B4, SIGMA) (PC). The effect of the tested substances upon TNF-α secretion was investigated after adding them into cultures of cells stimulated by LPS (TS). The TNF-α level in the cell supernatant was determined by ELISA procedure according to the suggestions of the producer (R&D Systems). The test sensitivity was <3 pg/ml TNF-α. The IL-1 level was determined in an assay under the same conditions and with the same number of cells and the same concentration of the stimulus by ELISA procedure (R&D Systems). The percentage of inhibition of TNF-α or IL-1 production was calculated by the equation:

% inhibition=[1−(TS−NC)/(PC−NC)]*100.

The IC-50 value was defined as the substance concentration, at which 50% of TNF-α production were inhibited.

Compounds showing IC-50 with 20 μM or lower concentrations are active.

Determination of TNF-α and IL-1 Secretion in Mouse Peritoneal Macrophages In Vitro In order to obtain peritoneal macrophages, Balb/C mouse strain males, age 8 to 12 weeks, were injected i.p. with 300 μg of zymosan (SIGMA) dissolved in a phosphate buffer (PBS) in a total volume of 0.1 ml/mouse. After 24 hours the mice were euthanized according to the Laboratory Animal Welfare Act. The peritoneal cavity was washed with a sterile physiological solution (5 ml). The obtained peritoneal macrophages were washed twice with a sterile physiological solution and, after the last centrifugation (350 g/10 min), resuspended in RPMI 1640, into which 10% of FBS were added. In order to determine TNF-α secretion, $5 \times 10^4$ cells/well were cultivated in a total volume of 200 μl for 18 to 24 hours on microtitre plates with a flat bottom (96 wells, Falcon) in RPMI 1640 medium, into which 10% FBS (Fetal Bovine Serum, Biowhittaker) inactivated by heat, 100 units/ml of penicillin, 100 mg/ml of streptomycin, 20 mM HEPES and 50 μM 2-mercaptoethanol (all of GIBCO) were added. The cells were incubated at 37° C. in an atmosphere with 5% $CO_2$ and 90% humidity. In a negative control the cells were cultivated only in a medium (NC), whereas in a positive control the TNF-α secretion was triggered by adding 10 ng/ml of lipopolysaccharides (LPS, E. coli serotype 0111: B4, SIGMA) (PC). The effect of the substances upon the TNF-α secretion was investigated after adding them into cultures of cells stimulated with LPS (TS). The TNF-α level in the cell supernatant was determined by ELISA procedure specific for TNF-α and IL-1 (R&D Systems, Biosource). The percentage of inhibition of TNF-α or IL-1 production was calculated by the equation:

% inhibition=[1−(TS−NC)/(PC−NC)]*100.

The IC-50 value was defined as the substance concentration, at which 50% of TNF-α production were inhibited.

Compounds showing IC-50 with 10 μM or lower concentrations are active.

In vivo Model of LPS-Induced Excessive TNF-α or IL-1 Secretion in Mice

TNF-α or IL-1 secretion in mice was induced according to the already disclosed method (Badger A M et al., *J. Pharmac. Env. Therap.*, 1996, 279:1453–1461). Balb/C males, age 8 to 12 weeks, in groups of 6 to 10 animals were used. The animals were treated p.o. either with a solvent only (in negative and in positive controls) or with solutions of substances 30 minutes prior to i.p. treatment with LPS (E.

coli serotype 0111:B4, Sigma) in a dosis of 1–25 µg/animal. Two hours later the animals were euthanized by means of i.p. Roumpun (Bayer) and Ketanest (Parke-Davis) injection. A blood sample of each animal was taken into a Vacutainer tube (Becton Dickinson) and the plasma was separated according to the producer's instructions. The TNF-α level in the plasma was determined by ELISA procedure (Biosource, R&D Systems) according to the producer's instructions. The test sensitivity was <3 µg/ml TNF-α. The IL-1 level was determined by ELISA procedure (R&D Systems). The percentage of inhibition of TNF-α or IL-1 production was calculated by the equation:

% inhibition=[1−(TS−NC)/(PC−NC)]*100.

Active are the compounds showing 30% or more inhibition of TNF-α production at a dosis of 10 mg/kg.

Writhing Assay for Analgetic Activity

In this assay pain is induced by the injection of an irritant, most frequently acetic acid, into the peritoneal cavity of mice. Animals react with characteristic writhings, which has given the name to the assay (Collier HOJ et al., *Pharmac. Chemother.*, 1968, 32:295–310; Fukawa K et al., *J. Pharmacol. Meth.*, 1980, 4:251–259; Schweizer A et al., *Agents Actions*, 1988, 23:29–31). The assay is convenient for the determination of analgetic activity of compounds. Procedure: male Balb/C mice (Charles River, Italy), age 8 to 12 weeks, were used. A control group received methyl cellulose p.o. 30 minutes prior to i.p. application of acetic acid in a concentration of 0.6%, whereas test groups received standard (acetylsalicylic acid) or test substances in methyl cellulose p.o. 30 minutes prior to i.p. application of 0.6% acetic acid (volume 0.1 ml/10 g). The mice were placed individually under glass funnels and the number of writhings was registered for 20 minutes for each animal. The percentage of writhing inhibition was calculated according to the equation:

% inhibition=(mean value of number of writhings in the control group−number of writhings in the test group)/number of writhings in the control group*100.

Active are the compounds showing such analgetic activity as acetylsalicylic acid or better.

In Vivo Model of LPS-Induced Shock in Mice

Male Balb/C mice (Charles River, Italy), age 8 to 12 weeks, were used. LPS isolated from *Serrathie marcessans* (Sigma, L-6136) was diluted in sterile physiological solution. The first LPS injection was administered intradermally in a dosis of 4 µg/mouse. 18 to 24 hours later, LPS was administered i.v. in a dosis of 90–200 µg/mouse. A control group received two LPS injections as disclosed above. The test groups received substances p.o. half an hour prior to each LPS application. Survival after 24 hours was observed.

Active are the substances at which the survival at a dosis of 30 mg/kg was 40% or more.

Compounds from Examples 5 to 7 show activity in at least two investigated assays though these results only represent an illustration of the biological activity of compounds and should not limit the invention in any way.

EXAMPLE 1 a) 1H-8-Oxa-1-aza-dibenzo[e,h]azulene (4)

To an ethanolic solution of 11-[2-(dimethyl-hydrazono)-ethylidene]-11H-dibenzo[b,f]oxepine-10-one (6.16 mmol in 47 mL), $Na_2S_2O_4$ (0.036 mol) and water (23 mL) were added. The reaction mixture was stirred under heating at boiling temperature for 3 to 4 hours. Then it was poured into an ice-water mixture and the product was extracted with dichloromethane. The crude product was purified by column chromatography and an oily product was isolated.

b) 11-Chloro-1H-8-oxa-1-aza-dibenzo[e,h]azulene (5)

According to the above process starting from 8-chloro-11-[2-(dimethyl-hydrazono)-ethylidene]-1H-dibenzo[b,f]oxepine-10-one a product in the form of an oil was obtained.

c) 1H-8-Thia-1-aza-dibenzo[e,h]azulene (6)

According to the above process, starting from 11-[2-(dimethyl-hydrazono)-ethylidene]-11H-dibenzo[b,f]thiepine-10-one an oily product was obtained.

EXAMPLE 2

1H-8-Oxa-1-aza-dibenzo[e,h]azulene-2-carbaldehyde (7)

To dimethylformamide (38.7 mmol) cooled to 0° C., phosphoric trichloride (25.7 mmol) was added drop by drop and then the reaction mixture was stirred at room temperature for 15 minutes. To the reaction mixture cooled again to 0° C., a dimethylformamide solution of 1H-8-oxa-1-aza-dibenzo[e,h]azulene (4, 2.57 mmol in 5 mL) was added. Then the reaction mixture was stirred at 70–80° C. for 1–2 hours, cooled to room temperature and, by adding 50% NaOH, the pH was adjusted to 8–9. Such alkaline solution was heated for 1 hour at 70° C., then cooled to room temperature and poured into an ice-water mixture. The organic product was extracted with ethyl acetate, purified by chromatography on silica gel column and a yellow oily product was isolated.

According to the above process, by formylation of the compounds 5 and 6 there were prepared the compounds 11-chloro-1H-8-oxa-J-aza-dibenzo[e,h]azulene-2-carbaldehyde (8) and 1H-8-thia-1-aza-dibenzo[e,h]azulene-2-carbaldehyde (9).

EXAMPLE 3

1-(2-Trimethylsilyl-ethoxymethyl)-1H-8-oxa-J-aza-dibenzo[e,h]azulene-2-carbaldehyde (10)

A tetrahydrofuran solution of 1H-8-oxa-1-aza-dibenzo[e,h]azulene-2-carbaldehyde (7; 1.9 mmol in 15 mL) was cooled to 0° C. and slowly sodium hydride (60% dispersion in mineral oil, 125 mg) was added thereto. The reaction mixture was stirred at 0° C. until hydrogen stopped to develop (15–30 minutes) and trimethylsilyl ethoxymethyl chloride, $(CH_3)_3SiCH_2CH_2OCH_2Cl$ (SEM-Cl; 2 mmol) was added to the cooled reaction mixture. The reaction mixture was stirred at room temperature for one hour and then it was diluted by addition of water. The organic product was extracted with ethyl acetate. After drying the organic extracts on anhydrous sodium sulfate and evaporating the solvent, the crude product was purified by chromatography on a silica gel column. A dark oily product was isolated.

According to the above process, by silylating the compounds 8 and 9 there were prepared the compounds 11-chloro-1-(2-trimethylsilyl-ethoxymethyl)-1H-8-oxa-1-aza-dibenzo[e,h]azulene-2-carbaldehyde (11) and 1-(2-trimethylsilyl-ethoxymethyl)-1H-8-thia-1-aza-dibenzo[e,h]azulene-2-carbaldehyde (12).

EXAMPLE 4

[1-(2-Trimethylsilyl-ethoxymethyl)-1H-8-oxa-1-aza-dibenzo[e,h]azulene-2-yl]-methanol (13)

To a methanolic solution of 1-(2-trimethylsilanyl-ethoxymethyl)-1H-8-oxa-1-aza-dibenzo[e,h]azulene-2-carbaldehyde (10; 2.45 mmol in 25 mL), NaBH₄ (4 mmol) was added and the reaction mixture was stirred at room temperature for 2 hours. Then the pH of the reaction mixture was adjusted to 5 by adding acetic acid, the solvent was evaporated to dryness and the dry residue was extracted with ethyl acetate. By purifying the crude product by chromatography on a silica gel column an oily product was isolated.

According to the above process, by reacting the compounds 11 and 12 with NaBH₄ there were prepared the compounds
[11-chloro-1-(2-trimethylsilyl-ethoxymethyl)-1H-8-oxa-1-aza-dibenzo[e,h]azulene-2-yl]-methanol (14) and
[1-(2-trimethylsilyl-ethoxymethyl)-J H-8-thia-1-aza-dibenzo[e,h]azulene-2-yl]-methanol (15).

extracted with dichloromethane. The organic extract was washed with water, dried on anhydrous Na₂SO₄ and evaporated under reduced pressure. After purifying the evaporated residue by chromatography on a silica gel column, dimethyl-{2-[1-(2-trimethylsilyl-ethoxymethyl)-1H-8-oxa-1-aza-dibenzo[e,h]azulene-2-ylmethoxy]-ethyl}-amine was isolated in the form of an oil;

MS (m/z): 465.4 [MH]⁺.

To a solution of the silyl compound prepared above (0.11 mmol) in tetrahydrofuran (1 mL) tetrabutylammonium fluoride (5 mmol, 1M solution in THF) was added. The reaction mixture was heated for 5 hours at boiling temperature and then it was cooled to room temperature, diluted with diethyl ether and washed with water. The organic extracts were

TABLE 1

I

| cmp. | X | Y | Z | R¹ | R² | MS(m/z) | ¹H NMR(ppm, CDCl₃) |
|---|---|---|---|---|---|---|---|
| 4 | O | H | H | H | H | 231.9[M − H]⁻ | 6.59(t, 1H); 6.97(t, 1H); 7.15–7.49(m, 8H); 8.48(bs, 1H) |
| 5 | O | H | 11-Cl | H | H | 2.66[M − H]⁻ | 6.58(t, 1H); 6.97(t, 1H); 7.16–7.25(m, 6H); 7.47(m, 1H); 8.49(bs, 1H) |
| 6 | S | H | H | H | H | 250[MH]⁺ | 6.61(t, 1H); 6.99(t, 1H); 7.20–7.65(m, 8H); 8.54(bs, 1H) |
| 7 | O | H | H | CHO | H | 262.2[MH]⁺ | 7.19–7.52(m, 9H); 9.83(s, 1H) |
| 8 | O | H | 11-Cl | CHO | H | 353 [M + Na⁺ + MeOH] | — |
| 9 | S | H | H | CHO | H | 298[M + Na⁺] | 7.27–7.69(m, 8H); 8.04(bs, 1H); 9.67(s, 1H) |
| 10 | O | H | H | CHO | SEMᵃ | 414.1[M + Na⁺] | 0.03(s, 9H); 0.99(m, 2H); 3.83(m, 2H); 5.38(s, 2H); 7.23–7.53(m, 8H); 8.02(m, 1H); 9.74(m, 1H) |
| 11 | O | H | 11-Cl | CHO | SEM | 448.4[M + Na⁺] | 0.024(s, 9H); 0.92–1.09(m, 2H); 3.50–3.99(m, 2H); 5.37(s, 2H); 7.20–8.07(m, 8H); 9.74(s, 1H) |
| 12 | S | H | H | CHO | SEM | 430.1[M + Na⁺] | 0.02(s, 9H); 0.93(t, 2H); 3.55–3.75(dm, 2H); 5.53(d, 1H); 5.93(d, 1H); 7.27–7.8(m, 9H); 10.04(s, 1H) |
| 13 | O | H | H | CH₂OH | SEM | 393.2[MH]⁺ | 0.025(s, 9H); 0.97(t, 2H); 1.59(bs, 1H); 3.64(m, 2H); 4.79(s, 2H); 5.48(s, 2H); 6.6(s, 1H); 7.19–7.52(m, 8H) |
| 14 | O | H | 11-Cl | CH₂OH | SEM | 450 [M + Na⁺]; 410 [M − OH] | 0.04(s, 9H); 1.07(m, 2H); 1.57(s, 1H); 3.69(m, 2H); 4.77(s, 2H); 5.39(s, 2H); 6.56(s, 1H); 7.18–7.31(m, 5H); 7.46(m, 1H); 7.55(d, 1H) |
| 15 | S | H | H | CH₂OH | SEM | 432.1[M + Na⁺]; 392.1[M − OH] | 0.02(s, 9H); 0.93(m, 2H); 1.6(bs, 1H); 3.33–3.62(dm, 2H); 4.82(s, 2H); 5.47(s, 2H); 6.61(s, 1H); 7.23–7.74(m, 8H) |

ᵃSEM = (CH₃)₃SiCH₂CH₂OCH₂

EXAMPLE 5 a) Dimethyl-{2-[1-(2-trimethylsilyl-ethoxymethyl)-1H-8-oxa-1-aza-dibenzo[e,h]azulene-2-ylmethox]-ethyl}-amine (I; X=O, Y=Z=H, R¹=(CH₃)₂N(CH₂)₂OCH₂, R²=(CH₃)₃Si(CH₂)2OCH₂)

Dimethyl-[2-(1H-8-oxa-1-aza-dibenzo[e,h]azulene-2-ylmethoxy)-ethyl]-amine (I; X=O, Y=Z=H, R¹=(CH₃)₂N(CH₂)₂OCH₂, R²=H)

To a solution of 2-dimethylaminoethyl chloride hydrochloride (5.2 mmol) in 50% sodium hydroxide (10 mL), benzyl triethyl amrnmonium chloride (a catalytic amount) and a solution of the alcohol 13 (0.3 mmol) in toluene (15 mL) were added. The reaction mixture was heated under vigorous stirring at boiling temperature for 3 hours. Then it was cooled to room temperature, diluted with water and dried on anhydrous Na₂SO₄, the solvent was evaporated under reduced pressure and the crude product was purified by chromatography on a silica gel column. After purifying a light yellow oily dimethyl-[2-(1H-8-oxa-1-aza-dibenzo[e,h]azulene-2-ylmethoxy)-ethyl]-amine was isolated; MS (m/z): 357.4 [M+Na⁺].

b) Dimethyl-{3-[1-(2-trimethylsilyl-ethoxymethyl)-1H-8-oxa-1-aza-dibenzo[e,h]azulene-2-ylmethoxy]-propyl}-amine (I; X=O, Y=Z=H, R²=(CH₃)₂N(CH₂)₃OCH₂, R²=(CH₃)₃Si(CH₂)₂OCH₂)

Dimethyl-[3-(1H-8-oxa-1-aza-dibenzo[e,h]azulene-2-ylmethoxy)-propyl]-amine (I; X=O, Y=Z=H, R¹=(CH₃)₂N(CH₂)₃OCH₂, R²=H)

By a reaction of the alcohol 13 (0.3 mmol) and 3-dimethylaminopropyl chloride hydrochloride (4.7 mmol), dimethyl-{3-[1-(2-trimethylsilyl-ethoxymethyl)-1H-8-oxa-1-aza-dibenzo[e,h]azulene-2-ylmethoxy-propyl}-amine was obtained according to the process disclosed in Example 5a in the form of a light yellow oily product.

MS (m/z): 479.4 [MH]$^+$.

After the removal of the N-protecting group according to the process disclosed in Example 5a and purifying the product by chromatography on a silica gel column, dimethyl-[3-(1H-8-oxa-1-aza-dibenzo[e,h]azulene-2-ylmethoxy)-propyl]-amine in the form of a light yellow oily product was obtained;

MS (m/z): 349.4 [MH]$^+$.

EXAMPLE 6 a) {2-[11-Chloro-1-(2-trimethylsilyl-ethoxymethyl)-]H-8-oxa-1-aza-dibenzo[e,h]azulene-2-ylmethoxy-ethyl}-dimethyl-amine (1; X=O, Y=H, Z=11-Cl, R$^1$=(CH$_3$)$_2$N(CH$_2$)$_2$OCH$_2$, R$^2$=(CH$_3$)$_3$Si(CH$_2$)$_2$OCH$_2$)

[2-(11-Chloro-1H-8-oxa-1-aza-dibenzo[e,h]azulene-2-ylmethoxy)-ethyl]-dimethyl-amine (I; X=O, Y=H, Z=11-Cl, R$^1$=(CH$_3$)$_2$N(CH$_2$)$_2$OCH$_2$, R$^2$=H)

To a solution of 2-dimethylaminoethyl chloride hydrochloride (5.2 mmol) in 50% sodium hydroxide (10 mL), benzyltriethyl ammonium chloride (a catalytic amount) and a solution of the alcohol 14 (0.28 mmol) in toluene (10 mL) were added. The reaction mixture was heated under vigorous stirring at boiling temperature for 4 hours. Then it was cooled to room temperature, diluted with water and extracted with dichloromethane. The organic extract was washed with water, dried on anhydrous Na$_2$SO$_4$ and evaporated under reduced pressure. After purifying the evaporated residue, {2-[11-chloro-1-(2-trimethylsilyl-ethoxymethyl)-1H-8-oxa-1-aza-dibenzo[e,h]azulene-2-ylmethoxy]-ethyl}-dimethyl-amine was isolated by chromatography on silica gel column in the form of an oily product;

MS (m/z): 499.2 (MH$^+$).

After the removal of the N-protecting group according to the process disclosed in Example 5a and purifying the product by column chromatography, [2-(11-chloro-1H-8-oxa-1-aza-dibenzo[e,h]azulene-2-ylmethoxy)-ethyl]-dimethyl-amine in the form of a light yellow oil was obtained;

MS (m/z): 369.2 [MH]$^+$.

b) {3-[J1-Chloro-1-(2-trimethylsilyl-ethoxymethyl)-1H-8-oxa-1-aza-dibenzo[e,h]azulene-2-ylmethoxy]-propyl)-dimethyl-amine (I; X=O, Y=H, Z=11-Cl, R$^1$=(CH$_3$)$_2$N(CH$_2$)$_3$OCH$_2$, R$^2$=(CH$_3$)$_3$Si(CH$_2$)$_2$OCH$_2$)

[3-(11-Chloro-1H-8-oxa-1-aza-dibenzo[e,h]azulene-2-ylmethoxy)-propyl]-dimethyl-amine (I; X=O, Y=H, Z=11-Cl, R$^1$=(CH$_3$)$_2$N(CH$_2$)$_3$OCH$_2$, R$^2$=H)

By reacting the alcohol 14 (0.28 mmol) and 3-dimethylaminopropyl chloride hydrochloride (4.7 mmol) according to the process disclosed in Example 5a, (3-[f]-chloro-1-(2-trimethylsilyl-ethoxymethyl)-1H-8-oxa-1-aza-dibenzo[e,h]azulene-2-ylmethoxy]-propyl}-dimethyl-amine in the form of a light oily product was obtained;

MS (m/z): 513.2 [MH]$^+$.

After the removal of the N-protecting group according to the process disclosed in Example 5a and purifying the product by chromatography on a silica gel column, [3-(11-chloro-1H-8-oxa-1-aza-dibenzo[e,h]azulene-2-ylmethoxy)-propyl]-dimethyl-amine in the form of a light oil was obtained;

MS (m/z): 383.2 [MH]$^+$.

EXAMPLE 7 a) Dimethyl-{2-[1-(2-trimethylsilyl-ethoxymethyl)-1H-8-thia-1-aza-dibenzo[e,h]azulene-2-ylmethoxy]-ethyl}-amine (I, X=S, Y=Z=H, =(CH$_3$)$_2$N(CH$_2$)$_2$ OCH$_2$, R$^2$=(CH$_3$)$_3$Si(CH$_2$)$_2$OCH$_2$)

Dimethyl-[2-(1H-8-thia-1-aza-dibenzo[e,h]azulene-2-ylmethoxy)-ethyl]-amine (I; X=S, Y=Z=H, R$^1$=(CH$_3$)$_2$N(CH$_2$)2OCH$_2$, R$^2$=H)

To a solution of 2-dimethylaminoethyl chloride hydrochloride (5.2 mmol) in 50% sodium hydroxide (10 mL), benzyltriethyl ammonium chloride (a catalytic amount) and a solution of the alcohol 15 (0.39 mmol) in toluene (15 mL) were added. The reaction mixture was heated under vigorous stirring at boiling temperature for 4 hours. Then it was cooled to room temperature, diluted with water and extracted with dichloromethane. The organic extract was washed with water, dried on anhydrous Na$_2$SO$_4$ and evaporated under reduced pressure. After purifying the evaporated residue, dimethyl-{2-[1-(2-trimethylsilyl-ethoxymethyl)-1H-8-thia-1-aza-dibenzo[e,h]azulene-2-ylmethoxy]-ethyl}-amine was isolated by chromatography on a silica gel column in the form of an oil;

MS (m/z): 480.9 [MH]$^+$.

After the removal of the N-protecting group according to the process disclosed in Example 5a and purifying the product by chromatography on a silica gel column, dimethyl-[2-(1H-8-thia-1-aza-dibenzo[e,h]azulene-2-ylmethoxy)-ethyl]-amine was obtained in the form of an oil;

$^1$H NMR (ppm, CDCl$_3$): 2.39 (s, 6H); 2.72 (m, 2H); 3.74 (m, 2H); 4.70 (s, 2H); 6.42 (s, 1H); 7.18–7.61 (m, 8H); 11.06 (s, 1H);

MS (m/z): 351.1 [MH]$^+$.

b) Dimethyl-{3-[1-(2-trimethylsilyl-ethoxymethyl)-1H-8-thia-1-aza-dibenzo[e,h]azulene-2-ylmethoxy]-propyl}-amine (I, X=S, Y=Z=H, R$^1$=(CH$_3$)$_2$N(CH$_2$)$_3$OCH$_2$, R$^2$=(CH$_3$)$_3$Si(CH$_2$)$_2$OCH$_2$)

Dimethyl-[3-(1H-8-thia-1-aza-dibenzo[e,h]azulene-2-ylmethoxy)-propyl]-amine (I; X=S, Y=Z=H, R$^1$=(CH$_3$)$_2$N(CH)$_3$OCH$_2$, R$^2$=H)

By reacting the alcohol 15 (0.39 mmol) and 3-dimethylaminopropyl chloride hydrochloride (4.7 mmol) according to the process disclosed in Example 5a, dimethyl-{3-[1-(2-trimethylsilyl-ethoxymethyl)-1H-8-thia-1-aza-dibenzo[e,h]azulene-2-ylmethoxy]-propyl}-amine was obtained in the form of an oil;

$^1$H NMR (ppm, CDCl$_3$): 0.049 (s, 9H); 0.87 (m, 2H); 1.96–2.04 (m, 2H); 2.47 (s, 6H); 2.67 (m, 2H); 3.27–3.58 (dm, 2H); 3.67 (m, 2H); 4.73 (m, 2H); 5.47 (m, 2H); 6.59 (s, 1H); 7.24–7.75 (m, 8H);

MS (m/z): 495.2 [MH]$^+$.

19

After the removal of the N-protecting group according to the process disclosed in Example 5a and purifying the product by chromatography on a silica gel column, dimethyl-[3-(1H-8-thia-1-aza-dibenzo[e,h]azulene-2-ylmethoxy)-propyl]-amine was obtained in the form of an oil;

$^1$H NMR (ppm, CDCl$_3$): 1.78–1.86 (m, 2H); 2.23 (s, 6H); 2.45 (t, 2H); 3.62 (t, 2H); 4.63 (s, 2H); 6.45 (s, 1H); 7.18–7.62 (m, 8H); 9.8 (s, 1H);

MS (m/z): 365.1 [MH]$^+$.

c) 3-[1-(2-Trimethylsilyl-ethoxymethyl)-1H-8-thia-1-aza-dibenzo[e,h]azulene-2-ylmethoxy]-propylamine (I, X=S, Y=Z=H, R$^1$=H$_2$N(CH$_2$)$_3$OCH$_2$, R$^2$=(CH$_3$)$_3$Si(CH$_2$)$_2$OCH$_2$)

3-(1H-8-Thia-1-aza-dibenzo[e,h]azulene-2-ylmethoxy)-propylamine (1; X=S, Y=Z=H, R$^1$=H$_2$N(CH$_2$)$_3$OCH$_2$, R$^2$=H)

By reacting the alcohol 15 (0.39 mmol) and 3-aminopropyl chloride hydrochloride (5.8 mmol) according to the process disclosed in Example 5a, 3-[1-(2-trimethylsilyl-ethoxymethyl)-1H-8-thia-1-aza-dibenzo[e,h]azulene-2-ylmethoxy]-propylamine was obtained in the form of an oil;

MS (m/z): 466.9 [MH]$^+$.

After the removal of the N-protecting group according to the process disclosed in Example 5a and purifying the product by chromatography on a silica gel column, 3-(1H-8-thia-1-aza-dibenzo[e,h]azulene-2-ylmethoxy)-propylamine was obtained in the form of an oil;

MS (m/z): 336[MH]$^+$; 335 [M–H]$^-$.

Preparation of Starting compounds

11-[2-(dimethyl-hydrazono)-ethylidene]-11H-dibenzo[b,f]oxepine-10-one (1)

A mixture of 11H-dibenzo[b,f]oxepine-10-one (9.52 mmol) and glyoxal-mono(dimethylhydrazone) (9.52 mmol) was dissolved in ethanol (25 mL) and to the solution a freshly prepared ethanolic solution of sodium ethoxide (9.52 mmol Na in 25 mL of ethanol) was added drop by drop. The reaction mixture was stirred under heating at boiling temperature for 2 to 3 hours, then cooled to room temperature and poured to an ice-water mixture. Then the organic product was extracted with ethyl acetate, the organic extracts were dried on anhydrous Na$_2$SO$_4$ and, after evaporating the solvent, the crude product was purified by chromatography on a silica gel column. An oily brown product (a mixture of configuration isomers) was isolated;

MS (m/z): 293 [MH]$^+$.

Starting from 8-chloro-11H-dibenzo[b,f]oxepine-10-one there was formed 8-chloro-11-[2-(dimethyl-hydrazono)-ethylidene]-11H-dibenzo[b,f]oxepine-10-one (2), which was obtained in the form of an oil;

MS (m/z): 349.1 [M+Na$^+$].

Starting from 11H-dibenzo[b,f]thiepine-10-one there was formed 11-[2-(dimethyl-hydrazono)-ethylidene]-11H-dibenzo[b,f]thiepine-10-one (3) in the form of an oil;

MS (m/z): 331 [M+Na$^+$].

20

What is claimed is:
1. Compound of the formula I:

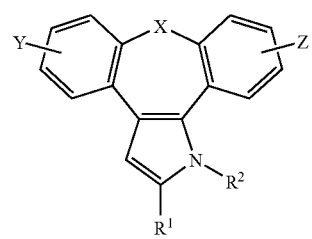

wherein
X is O, S, S(=O), or S(=O2);
Y and Z are each independently selected from the group consisting of hydrogen, halogen, C$_1$–C$_4$ alkyl, C$_2$–C$_4$ alkenyl, C$_2$–C$_4$alkynyl, halo-C$_1$–C$_4$alkyl, hydroxy, C$_1$–C$_4$ alkoxy, trifluoromethoxy, C$_1$–C$_4$alkanoyl, amino, amino-C$_1$–C$_4$alkyl, C$_1$–C$_4$alkylamino, N-(C$_1$–C$_4$-alkyl)amino, N,N-di(C$_1$–C$_4$-alkyl)amino, thiol, C$_1$–C$_4$alkylthio, sulfonyl, C$_1$–C$_4$ alkylsulfonyl, sulfinyl, C$_1$–C$_4$alkylsulfinyl, carboxy, C$_1$–C$_4$alkoxycarbonyl, cyano, and nitro;
R$^1$ is selected from the group consisting of hydrogen, halogen, an optionally substituted C$_1$–C$_7$alkyl or C$_2$–C$_7$ alkenyl, C$_2$–C$_7$ alkynyl, an optionally substituted aryl or heteroaryl, a heterocycle, hydroxy, hydroxy-C$_2$–C$_7$ alkenyl, hydroxy-C$_2$–C$_7$ alkynyl, C$_1$–C$_7$ alkoxy, thiol, thio-C$_2$–C$_7$ alkenyl, thio-C$_2$–C$_7$ alkynyl, C$_1$–C$_7$ alkylthio, amino, N-(C$_1$–C$_7$)alkylamino, N,N-di(C$_1$–C$_7$-alkyl)amino, (C$_1$–C$_7$-alkyl)amino, amino-C$_2$–C$_7$ alkenyl, amino-C$_2$–C$_7$ alkynyl, amino-C$_1$–C$_7$ alkoxy, C$_1$–C$_7$ alkanoyl, aroyl, oxo-C$_1$–C$_7$ alkyl, C$_1$–C$_7$ alkanoyloxy, carboxy, an optionally substituted C$_{1-7}$ alkyloxycarbonyl or aryloxycarbonyl, carbamoyl, N-(C$_1$–C$_7$-alkyl)carbamoyl, N,N-di(C$_1$–C$_7$-alkyl)carbamoyl, cyano, cyano-C$_1$–C$_7$ alkyl, sulfonyl, C$_1$–C$_7$ alkylsulfonyl, sulfinyl, C$_1$–C$_7$ alkylsulfinyl, nitro, and a substituent of the formula II:

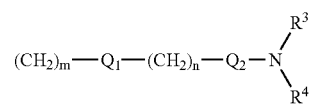

wherein
R$^3$ and R$^4$ an each independently selected from the group consisting of hydrogen, C$_1$–C$_4$alkyl, aryl or together with the nitrogen atom to which they are attached form an optionally substituted heterocycle or heteroaryl;
m and n are each an integer from 0 to 3;
Q$_1$ and Q$_2$ are each independently selected from the group consisting of oxygen, sulfur, and the groups

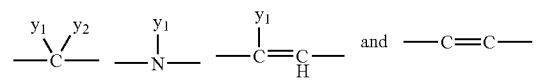

wherein y$_1$ and y$_2$ are each independently selected from the group consisting of hydrogen, halogen, an optionally substituted C$_1$–C$_4$alkyl or aryl, hydroxy, C$_1$C$_4$ alkoxy, $C_1$–$C_4$alkanoyl, thiol, $C_1$–$C_4$ alkylthio, sulfonyl, $C_1$–$C_4$alkylsulfonyl, sulfinyl, $C_1$–$C_4$ alkylsulfinyl, cyano, and nitro or $y_1$ and $y_2$ taken together with the carbon atom to which they are attached form a carbonyl or imino group;

$R^2$ is selected from the group consisting of hydrogen, optionally substituted $C_1$–$C_7$ alkyl or aryl, and a protecting group selected from the group consisting of formyl, $C_{1-7}$ alkanoyl, $C_1$–$C_7$ alkoxycarbonyl, arylalkyloxycarbonyl, aroyl, arylalkyl, $C_1$–$C_7$ alkylsilyl, and $C_1$–$C_7$ alkylsilyl-alkoxy-alkyl;

and pharmaceutically acceptable salts and solvates thereof.

2. The compound of claim 1, wherein X is S or O.

3. The compound of claim 2, wherein Y is H and Z is H or Cl.

4. The compound of claim 3, wherein $R^1$ is H, CHO, or $CH_2OH$, and $R^2$ is H or $(CH_3)_3Si(CH_2)_2OCH_2$.

5. The compound of claim 3, wherein $R^1$ is

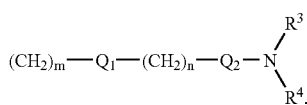

II

6. The compound of claim 5, wherein m is 1, $Q_1$ is O, n is 1 or 2, $Q_2$ is $CH_2$, $R^2$ is H or $(CH_3)_3Si(CH_2)_2OCH_2$, and $R^3$ and $R^4$ are each independently H or $CH_3$.

7. The compound of claim 4 selected from the group consisting of:
1H-8-oxa-1-aza-dibenzo[e,h]azulene;
11-chloro-1H-8-oxa-1-aza-dibenzo[e,h]azulene;
1H-8-thia-1-aza-dibenzo[e,h]azulene;
1H-8-oxa-1-aza-dibenzo[e,h]azulene-2-carbaldehyde;
11-chloro-1H-8-oxa-1-aza-dibenzo[e,h]azulene-2-carbaldehyde;
1H-8-thia-1-aza-dibenzo[e,h]azulene-2-carbaldehyde;
1-(2-trimethylsilyl-ethoxymethyl)-1H-8-oxa-1-aza-dibenzo[e,h]azulene-2-carbaldehyde;
11-chloro-1-(2-trimethylsilyl-ethoxymethyl)-1H-8-oxa-1-aza-dibenzo[e,h]azulene-2 carbaldehyde;
1-(2-trimethylsilyl-ethoxymethyl)-1H-8-thia-1-aza-dibenzo[e,h]azulene-2-carbaldehyde;
[1-(2-trimethylsilyl-ethoxymethyl)-1H-8-oxa-1-aza-dibenzo[e,h]azulene-2-yl]-methanol;
[11-chloro-1-(2-trimethylsilyl-ethoxymethyl)-1H-8-oxa-1-aza-dibenzo[e,h]azulene-2-yl]-methanol; and
[1-(2-trimethylsilyl-ethoxymethyl)-1H-8-thia-1-aza-dibenzo[e,h]azulene-2-yl]-methanol.

8. The compound of claim 6 selected from the group consisting of:
dimethyl-{2-[1-(2-trimethylsilyl-ethoxymethyl)-1H-8-oxa-1-aza-dibenzo[e,h]azulene-2-ylmethoxy]-ethyl}-amine;
dimethyl-[2-(1H-8-oxa-1-aza-dibenzo[e,h]azulene-2-ylmethoxy)-ethyl]-amine;
dimethyl-{3-[1-(2-trimethylsilyl-ethoxymethyl)-1H-8-oxa-1-aza-dibenzo[e,h]azulene-2-ylmethoxy]-propyl}-amine;
dimethyl-[3-(1H-8-oxa-1-aza-dibenzo[e,h]azulene-2-ylmethoxy)-propyl]-amine;
{2-[11-chloro-1-(2-trimethylsilyl-ethoxymethyl)-1H-8-oxa-1-aza-dibenzo[e,h]azulene-2-ylmethoxy]-ethyl}-dimethyl-amine;
[2-11-chloro-1H-8-oxa-1-aza-dibenzo[e,h]azulene-2-ylmethoxy)-ethyl]-dimethyl-amine;
{3-[11-chloro-1-(2-trimethylsilyl-ethoxymethyl)-1H-8-oxa-1-aza-dibenzo[e,h]azulene-2-ylmethoxy]-propyl}-dimethyl-amine;
[3-(11-chloro-IH-8-oxa-1-aza-dibenzo[e,h]azulene-2-ylmethoxy)-propyl]-dimethyl-amine;
dimethyl-{2-[1-(2-trimethylsilyl-ethoxymethyl)-1H-8-thia-1-aza-dibenzo[e,h]azulene-2-ylmethoxy]-ethyl}-amine;
dimethyl-[2-(1H-8-thia-1-aza-dibenzo[e,h]azulene-2-ylmethoxy)-ethyl]-amine;
dimethyl-{3-[1-(2-trimethylsilyl-ethoxymethyl)-1H-8-thia-1-aza-dibenzo[e,h]azulene-2-ylmethoxy]-propyl}-amine;
dimethyl-[3-(1H-8-thia-1-aza-dibenzo[e,h]azulene-2-ylmethoxy)-propyl]-amine;
3-[1-(2-trimethylsilyl-ethoxymethyl)-1H-8-thia-1-aza-dibenzo[e,h]azulene-2-ylmethoxy]-propylamine;
3-(1H-8-thia-1-aza-dibenzo[e,h]azulene-2-ylmethoxy)-propylamine;

and pharmaceutically acceptable salts thereof.

9. Process for the preparation of a compound of the formula I:

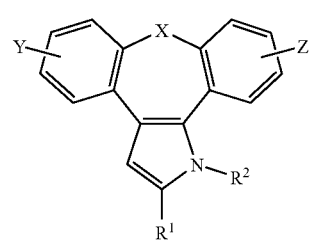

I wherein

X is O, S, S(=O), or S(=O)2;

Y and Z are each independently selected from the group consisting of hydrogen, halogen, $C_{1-4}$ alkyl, $C_2$–$C_4$ alkenyl, $C_2$–$C_4$ alkynyl, halo-$C_1$–$C_4$ alkyl, hydroxy, $C_1$–$C_4$ alkoxy, trifluoromethoxy, $C_1$–$C_4$ alkanoyl, amino, amino-$C_1$–$C_4$ alkyl, $C_1$–$C_4$ alkylamino, N-($C_1$–$C_4$-alkyl)amino, N,N-di($C_1$–$C_4$-alkyl)amino, thiol, $C_1$–$C_4$ alkylthio, sulfonyl, $C_1$–$C_4$ alkylsulfonyl, sulfinyl, $C_1$–$C_4$ alkylsulfinyl, carboxy, $C_1$–$C_4$ alkoxycarbonyl, cyano, nitro;

$R^1$ may be hydrogen, halogen, an optionally substituted $C_1$–$C_7$ alkyl or $C_2$–$C_7$ alkenyl, $C_2$–$C_7$ alkynyl, an optionally substituted aryl or heteroaryl and a heterocycle, hydroxy, hydroxy-$C_2$–$C_7$ alkenyl, hydroxy-$C_2$–$C_7$ alkinyl, $C_1$–$C_7$ alkoxy, thiol, thio-$C_2$–$C_7$ alkenyl, thio-$C_2$–$C_7$ alkinyl, $C_1$–$C_7$ alkylthio, amino, N-($C_1$–$C_7$) alkylamino, N,N-di($C_1$–$C_7$-alkyl)amino, ($C_1$–$C_7$-alkyl) amino, amino-$C_2$–$C_7$ alkenyl, amino-$C_2$–$C_7$ alkinyl, amino-$C_1$–$C_7$ alkoxy, $C_1$–$C_7$ alkanoyl, aroyl, oxo-$C_1$–$C_7$ alkyl, $C_1$–$C_7$ alkanoyloxy, carboxy, an optionally substituted $C_1$–$C_7$ alkyloxycarbonyl or aryloxycarbonyl, carbamoyl, N-($C_1$–$C_7$-alkyl)carbamoyl, N,N-di ($C_1$–$C_7$-alkyl)carbamoyl, cyano, cyano-$C_1$–$C_7$ alkyl, sulfonyl, $C_1$–$C_7$ alkylsulfonyl, sulfinyl, $C_1$–$C_7$ alkylsulfinyl, nitro, or a substituent of the formula II:

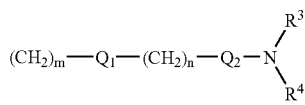

II wherein
R³ and R⁴ are each independently selected from the group consisting of hydrogen, $C_1$–$C_4$ alkyl, aryl or, together with the nitrogen atom to which they are attached, form an optionally substituted heterocycle or heteroaryl;

m and n represent an integer from 0 to 3;

$Q_1$ and $Q_2$ are each independently selected from the group consisting of oxygen, sulfur or groups:

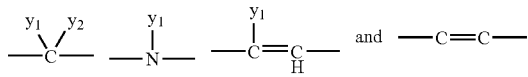

wherein the substituents
$y_1$, and $y_2$ are each independently selected from the group consisting of hydrogen, halogen, an optionally substituted $C_1$–$C_4$ alkyl or aryl, hydroxy, $C_1$–$C_4$ alkoxy, $C_1$–$C_4$ alkanoyl, thiol, $C_1$–$C_4$ alkylthio, sulfonyl, $C_1$–$C_4$ alkylsulfonyl, sulfinyl, $C_1$–$C_4$ alkylsulfinyl, cyano, nitro or $y_1$ and $y_2$ taken together with the carbon atom to which they are attached form a carbonyl or imino group;

R² is selected from the group consisting of hydrogen, optionally substituted $C_1$–$C_7$alkyl or aryl, and a protecting group selected from the group consisting of: formyl, $C_1$–$C_7$ alkanoyl, $C_1$–$C_7$ alkoxycarbonyl, arylalkyloxycarbonyl, aroyl, arylalkyl, $C_1$–$C_7$ alkylsilyl, and $C_1$–$C_7$ alkylsilyl-alkoxy-alkyl; and pharmacologically acceptable salts and solvates thereof, the process comprising:

a) for compounds of the formula I wherein R¹ is hydrogen, a cyclization of a compound of the formula III:

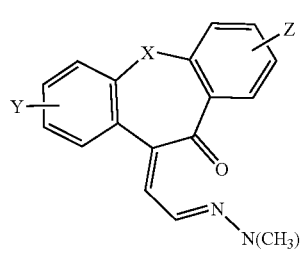

III b) for compounds of the formula I, wherein $Q_1$ is —O—, a reaction of an alcohol of the formula IV:

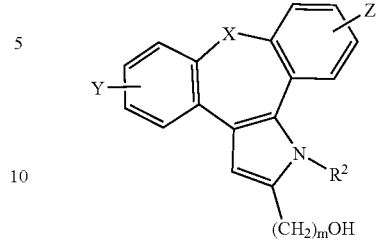

IV with a compound of the formula V:

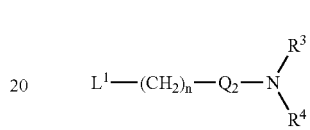

V wherein L¹ is a leaving group, c) for compounds of the formula I, wherein $Q_1$ is —O—, —NH—, —S— or —C≡C—, a reaction of a compound of the formula IVa:

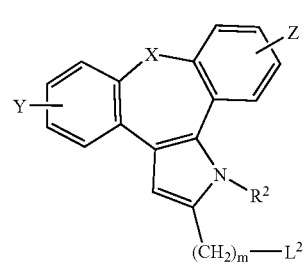

IVa wherein L² is a leaving group, with a compound of the formula Va:

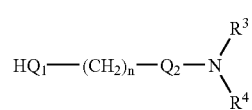

Va d) for compounds wherein $Q_1$ is —O—, —NH— or —S—, a reaction of a compound of the formula IVb:

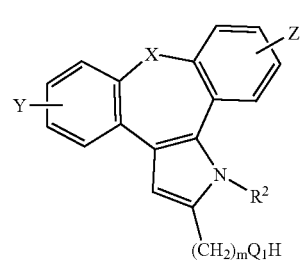

IVb with a compound of the formula V, wherein $L^1$ is a leaving group, e) for compounds wherein $Q_1$ is —C≡C—, a reaction of compound of the formula IVb, wherein $Q_1$ is carbonyl, with phosphorous ylides.

10. A method for treating inflammation associated with TNF-α comprising administering to a subject in need of treatment an effective amount of a compound according to claim 5.

11. The compound of claim 1, and pharmaceutically acceptable salts and solvates thereof, wherein $R^2$ is $(CH_3)_3Si(CH_2)_2OCH_2$.

12. The process of claim 9, wherein $R^2$ is $(CH_3)_3Si(CH_2)_2OCH_2$.

* * * * *

UNITED STATES PATENT AND TRADEMARK OFFICE
CERTIFICATE OF CORRECTION

PATENT NO. : 7,312,203 B2
APPLICATION NO. : 10/515679
DATED : December 25, 2007
INVENTOR(S) : Mercep et al.

It is certified that error appears in the above-identified patent and that said Letters Patent is hereby corrected as shown below:

Column 20, claim 1, line 37 should read:
-- alkanoyloxy, carboxy, an optionally substituted $C_1$-$C_7$ --

Column 20, claim 1, line 60 should read:

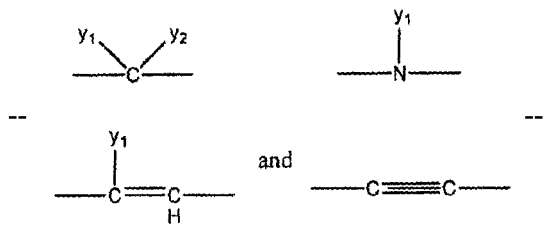

Column 20, claim 1, line 67 should read:
-- stituted $C_1$-$C_4$ alkyl or aryl, hydroxyl, $C_1$-$C_4$ alkoxy --

Column 21, claim 1, line 9 should read:
-- formyl, $C_1$-$C_7$ alkanoxyl, $C_1$-$C_7$ alkoxycarbonyl, aryla- --

Column 21, claim 7, line 43 should read:
-- 1-aza-dibenzo[e,h]azulene-2-carbaldehyde; --

Column 23, claim 9, line 25 should read:

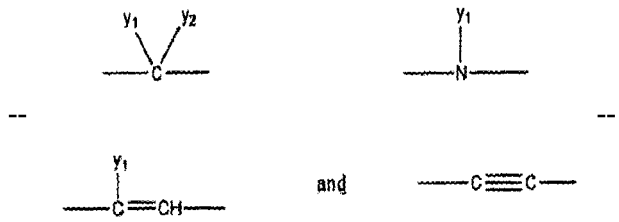

UNITED STATES PATENT AND TRADEMARK OFFICE
CERTIFICATE OF CORRECTION

PATENT NO. : 7,312,203 B2
APPLICATION NO. : 10/515679
DATED : December 25, 2007
INVENTOR(S) : Mercep et al.

It is certified that error appears in the above-identified patent and that said Letters Patent is hereby corrected as shown below:

Column 23, claim 9, line 37 should read:
-- or nitro or, --

Column 24, claim 9, line 26 should read:
-- -O-, -NH-, -S- or —C≡C—, a reaction of a --

Column 25, claim 9, line 3 should read:
-- e) for compounds wherein $Q_1$ is -C=C-, a reaction of a --

Signed and Sealed this

Second Day of September, 2008

JON W. DUDAS
*Director of the United States Patent and Trademark Office*